（12) United States Patent
Call

(10) Patent No.: US 7,291,131 B2
(45) Date of Patent: Nov. 6, 2007

(54) INFUSION SYRINGE

(75) Inventor: Evan W. Call, Bountiful, UT (US)

(73) Assignee: Physicians Industries, Inc., West Valley City, UT (US)

( * ) Notice: Subject to any disclaimer, the term of this patent is extended or adjusted under 35 U.S.C. 154(b) by 112 days.

(21) Appl. No.: 10/831,769

(22) Filed: Apr. 23, 2004

(65) Prior Publication Data

US 2005/0004518 A1 Jan. 6, 2005

Related U.S. Application Data

(63) Continuation-in-part of application No. 10/769,634, filed on Jan. 30, 2004.

(60) Provisional application No. 60/468,398, filed on May 5, 2003.

(51) Int. Cl.
*A61M 5/00* (2006.01)

(52) U.S. Cl. ...................... 604/187; 604/500

(58) Field of Classification Search ................ 604/187, 604/121, 131, 100.01, 67, 97, 181–186, 500
See application file for complete search history.

(56) References Cited

U.S. PATENT DOCUMENTS

| | | | |
|---|---|---|---|
| 3,625,793 A | 12/1971 | Sheridan | |
| 3,878,830 A | 4/1975 | Bicher | |
| RE30,365 E | 8/1980 | Mattler | |
| 4,370,982 A | 2/1983 | Reilly | |
| 4,439,185 A | 3/1984 | Lundquist | |
| 4,583,974 A | 4/1986 | Kokernak | |
| 4,651,738 A | 3/1987 | Demer et al. | |
| 4,655,749 A | 4/1987 | Fischione | |
| 4,710,179 A | 12/1987 | Haber et al. | |
| 4,723,938 A | 2/1988 | Goodin et al. | |
| 4,740,203 A | 4/1988 | Hoskins et al. | |
| 4,758,223 A | 7/1988 | Rydell | |
| 4,810,249 A | 3/1989 | Haber et al. | |
| 4,815,313 A * | 3/1989 | Beard .......................... 73/1.62 |
| 4,832,692 A | 5/1989 | Box et al. | |
| 4,919,121 A | 4/1990 | Rydell et al. | |
| 4,940,459 A | 7/1990 | Noce | |
| 4,951,677 A | 8/1990 | Crowley et al. | |
| 5,019,041 A | 5/1991 | Robinson et al. | |
| 5,047,015 A | 9/1991 | Foote et al. | |
| 5,057,078 A * | 10/1991 | Foote et al. ............. 604/99.01 |
| 5,084,060 A * | 1/1992 | Freund et al. .............. 606/192 |
| 5,137,514 A | 8/1992 | Ryan | |
| 5,147,300 A | 9/1992 | Robinson et al. | |
| 5,168,757 A | 12/1992 | Rabenau et al. | |
| 5,201,753 A | 4/1993 | Lampropoulos et al. | |
| 5,209,732 A | 5/1993 | Lampropoulos et al. | |
| 5,273,537 A | 12/1993 | Haskvitz et al. | |
| 5,383,855 A | 1/1995 | Nicholson et al. | |
| 5,385,549 A * | 1/1995 | Lampropoulos et al. ............. 604/100.03 |

(Continued)

*Primary Examiner*—Nicholas D. Lucchesi
*Assistant Examiner*—Christopher D. Koharski
(74) *Attorney, Agent, or Firm*—Kirton & McConkie; David B. Tingey

(57) ABSTRACT

A syringe configured for communication with a tubular member insertable into the body of a subject includes a pressure transducer integrally mounted in the plunger thereof, under a tip of the plunger, such that the force applied by the plunger to fluid within a barrel of the syringe is transmitted to the transducer. A resulting electronic signal is converted to a display value for aiding a physician.

19 Claims, 10 Drawing Sheets

U.S. PATENT DOCUMENTS

| | | |
|---|---|---|
| 5,387,194 A | 2/1995 | Williams et al. |
| 5,403,274 A | 4/1995 | Cannon |
| 5,425,713 A | 6/1995 | Taylor et al. |
| 5,429,606 A | 7/1995 | Robinson et al. |
| 5,431,629 A | 7/1995 | Lampropoulos et al. |
| 5,433,707 A | 7/1995 | Call |
| 5,449,344 A | 9/1995 | Taylor et al. |
| 5,449,345 A * | 9/1995 | Taylor et al. .......... 604/100.03 |
| 5,453,091 A * | 9/1995 | Taylor et al. .......... 604/100.03 |
| 5,458,571 A * | 10/1995 | Lampropoulos et al. .... 604/509 |
| 5,459,700 A | 10/1995 | Jacobs |
| 5,460,609 A | 10/1995 | O'Donnell |
| 5,472,424 A | 12/1995 | Lampropoulos et al. |
| 5,489,256 A | 2/1996 | Adair |
| 5,545,133 A | 8/1996 | Burns et al. |
| 5,562,614 A | 10/1996 | O'Donnell |
| 5,599,301 A | 2/1997 | Jacobs et al. |
| 5,625,144 A | 4/1997 | Chang |
| 5,647,847 A | 7/1997 | Lafontaine et al. |
| 5,685,848 A | 11/1997 | Robinson et al. |
| 5,695,468 A | 12/1997 | Lafontaine et al. |
| 5,704,913 A | 1/1998 | Abele et al. |
| 5,728,064 A | 3/1998 | Burns et al. |
| 5,741,229 A | 4/1998 | Robinson et al. |
| 5,749,853 A | 5/1998 | O'Donnell et al. |
| 5,752,935 A | 5/1998 | Robinson et al. |
| 5,785,685 A | 7/1998 | Kugler et al. |
| 5,808,203 A | 9/1998 | Nolan, Jr. et al. |
| 5,860,955 A | 1/1999 | Wright et al. |
| 5,891,089 A | 4/1999 | Katz et al. |
| 5,951,517 A | 9/1999 | Lampropoulos et al. |
| 5,968,017 A | 10/1999 | Lampropoulos et al. |
| 6,139,523 A | 10/2000 | Taylor et al. |
| 6,179,815 B1 | 1/2001 | Foote |
| 6,190,354 B1 | 2/2001 | Sell et al. |
| 6,245,043 B1 | 6/2001 | Villette |
| 6,394,977 B1 | 5/2002 | Taylor et al. |
| 6,792,306 B2 * | 9/2004 | Henley et al. ................. 604/20 |
| 2003/0216692 A1 * | 11/2003 | Fago et al. ................. 604/150 |
| 2004/0024361 A1 * | 2/2004 | Fago et al. ................. 604/152 |

* cited by examiner

INFUSION SYRINGE

CROSS-REFERENCE TO RELATED APPLICATION

This application is a continuation-in-part of U.S. application Ser. No. 10/769,634, filed Jan. 30, 2004, pending, which claims the benefit of U.S. Provisional Application Ser. No. 60/468,398, filed May 5, 2003, under 35 U.S.C. § 119(e), the contents of which are hereby incorporated in their entirety by this reference.

BACKGROUND OF THE INVENTION

1. Field of the Invention

This invention relates to an infusion syringe apparatus for applying and monitoring fluid pressure applied to the inter-vertebral disk of the spinal column, or more specifically, monitoring of the pressure applied through a needle or cannula through the annulus fibrosus of the disk and into the nucleus pulposus thus allowing the diagnosis of diseased or ruptured disks. The field may further include fluid pressure-inducing syringes and methods involved in percutaneous translumental angioplasty (PTA) procedures.

2. State of the Art

Infusers utilized in diskography and balloon angioplasty are well known and established in medical practice. The tools typically applied to angioplasty have found application in other fields as well, including opening diseased carotid arteries, improving or reestablishing blood flow to the extremities of diabetics, and similar procedures. Similar tools have been used in the field of pain diagnosis and management related to orthopedic procedures related to the spine.

The number of failed or ineffectual spine surgeries has driven the development of new techniques for verifying the location of damage or injury in the vertebral column. Typically, these procedures involve the insertion of a curved or specifically shaped cannula or needle under the transverse process of the vertebra and around the inferior articular process and penetrating the annulus fibrosus. Application of fluid pressure to the nucleus pulposus will either go undetected, create relief from chronic pain, or induce a pain episode due to the pinching of a nerve. By the application of this technique to suspect vertebral disks, a physician can identify the pain locus and, thus, use the appropriate intervention to provide relief for the patient. This process is typically performed utilizing ionic contrast media, typically made from ionically bound iodine. This media allows the physician to view the procedure on a fluoroscope, which aids in needle positioning and visual diagnosis. Diagnosis is based on the ability, or inability, of the end of inter-vertebral disks to contain the contrast media when it is injected under pressure into the nucleus pulposus of the disk.

Typically, any syringe with a mechanism for measuring pressure has been used to measure the patency of the inter-vertebral disk. However, such syringes typically utilize a transducer mounted at the distal end of the syringe barrel which is in communication with the fluid path of the syringe. The presence of a non-transparent transducer and associated fixtures adjacent the fluid path prevents clear vision of bubbles in the contrast media or other imperfections that may be of concern in interventional procedures. Such devices are described in U.S. Pat. Nos. 5,021,046 and 5,084,060. Also, many such devices are awkward to use, are unduly complex or fail to provide a flexible fluid pressure adjustment.

SUMMARY OF THE INVENTION

The present invention includes a hand-operated syringe for applying pressure to a fluid within the syringe. The pressurized fluid interacts, directly or indirectly, with some physiology of the human body.

The syringe has a barrel, which may be constructed from a rigid material and, optionally, may be transparent. A plunger adapted to slide within the barrel and to apply pressure to fluid within the barrel may be configured to have two operative motions: 1) a first, sliding motion induced by direct hand motion, e.g., thumb force, at the proximal end of the plunger or some plunger extension attached generally axially to the proximal end of the plunger, whereby a rapid increase or decrease in the fluid pressure can be controllably caused to occur within the syringe barrel and 2) a second motion wherein the plunger is not freely slidable but has threads which interact with an adjustment mechanism, wherein the adjustment mechanism is engageable and disengageable to permit minute axial motion of the plunger and, thus, adjustment of the applied fluid pressure in controlled micro pressure adjustments.

The adjustment mechanism includes means whereby the threads on the plunger may be rapidly (e.g., instantaneously) disengaged to permit the plunger to slide freely thereby releasing the fluid pressure within the syringe barrel. The adjustment mechanism engages threads on the plunger or on a casing (sleeve) associated with and enveloping at least a portion of the plunger's external surface.

Various features of the syringe enable a user to completely operate the syringe with a single hand, leaving the user's other hand free to perform other tasks.

A further feature of the syringe is a pressure monitoring system whereby the pressure of the fluid within the barrel may be observed and, by appropriate adjustment of the plunger, such pressure may be controllably increased, decreased, or released. The pressure monitoring system of the syringe may provide a user with one or more warnings when the pressure reaches a threshold value.

A pressure sensitive transducer is fitted to communicate directly, or indirectly, with the fluid within the syringe barrel. Such transducers have conventionally been attached to the barrel generally at or near the distal end of the barrel, as illustrated in U.S. Pat. Nos. 5,021,046, 5,009,662, and 5,004,472 to Wallace (hereinafter collectively referred to as "the Wallace Patents"). While such positioning of the pressure sensitive transducer is acceptable for many purposes, the transducer and its associated fittings are not transparent and block the syringe operator's vision of the fluid within the portion of the barrel adjacent the transducer. This may be very disadvantageous if air bubbles exist within the fluid within the syringe barrel or within the tubing leading to a patient's body especially where the fluid is intended to enter a portion of the body, such as occurs with fluid injection into a spinal disk.

A significant advantage is realized by attaching the transducer to the distal end (pressure tip) of the plunger and having at least a part of the electronics which are part of the pressure-monitoring apparatus contained within the plunger. A tip of the plunger in which the pressure transducer is positioned may be configured to cover, but accurately transmit pressure to, the pressure sensitive transducer.

Placement of the transducer and, optionally, electronics on the plunger is especially useful inasmuch as the electronics may emit a wireless signal to cause a pressure reading to occur on a remote display, i.e., a display located on the exterior of the syringe barrel, a remote display not attached to the syringe barrel, including a display positioned at or near the proximal end of the syringe plunger or an extension attached thereto, or a display which is remote from the entire syringe.

The display may alternatively interact with the electronics associated with the pressure transduced by an electrical conductor. For example, the pressure transducer may communicate, by wires, with electronics or a display that is permanently secured to a proximal end of the plunger, or with a electronics or a display that is configured to be detachably coupled to the syringe plunger.

The electronics may be configured to ensure that the pressure sensitive transducer is initially exposed to an appropriate amount of pressure and, if not, indicate that there is a problem with the syringe.

A memory element may be associated with the electronics to store and facilitate transfer of data generated by use of the pressure sensing transducer. In addition, or alternatively, the electronics of a syringe according to the present invention may be provided with a communication element that facilitates the transmission of data generated by the pressure sensing transducer to external electronic devices, such as computers.

Other features and advantages of the present invention will become apparent to those in the art through consideration of the ensuing description, the accompanying drawings, and the appended claims.

DETAILED DESCRIPTION OF THE INVENTION

Figure 1:
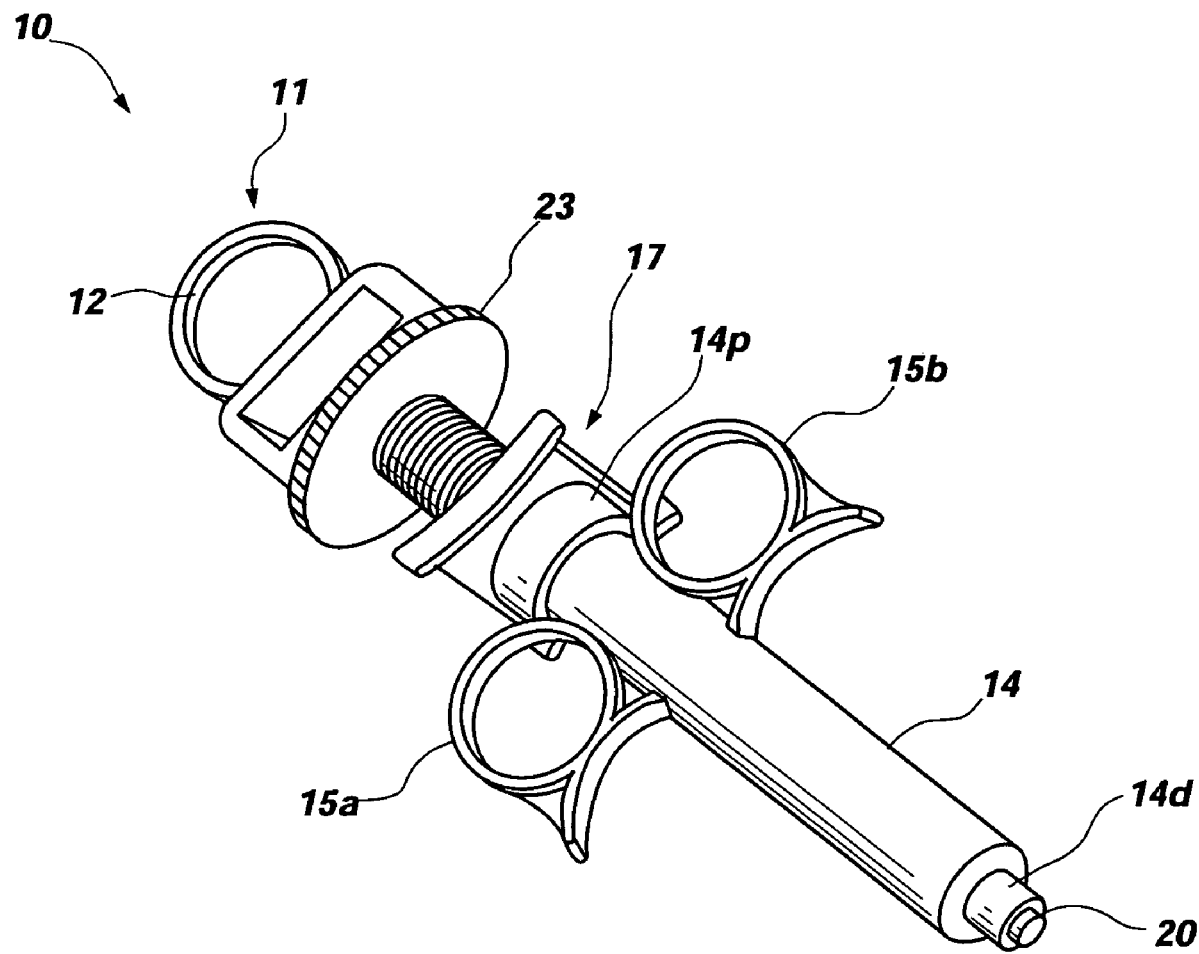
FIG. 1 is a perspective view of a syringe of the present invention.

FIG. 1 is an external perspective view of a syringe 10 that incorporates teachings of the present invention. Syringe 10 includes an elongate barrel 14 and a plunger 11 disposed within barrel 14.

Barrel 14, which may be configured similarly to other syringe barrels that are known in the art, includes a connection element 20, such as a luer lock or a slip socket type connection element, at a distal end 14d thereof. By way of example only, connection element 20 may be configured to secure a bonded extension line to barrel 14, in pressure-tight fluid communication therewith. Barrel 14 may also include rings or other grasping elements 15a and 15b at or near the proximal end 14p thereof. Grasping elements 15a and 15b may be held by the index finger and the middle finger of a health care professional (e.g., a physical or technician) or other individual who is using syringe 10.

Plunger 11 may have a ring or other grasping element 12 at the proximal end 11p thereof. Grasping element 12 of plunger 11 may be configured to facilitate manipulation of plunger 11 (e.g., longitudinal movement of plunger 11 through barrel 14 and, thus, the fluid pressure generated by syringe 10) with the thumb or other digit of an individual who is using syringe 10, or with automated apparatus for controlling the operation of syringe 10.

In the illustrated embodiment of syringe 10, grasping elements 12, 15a, and 15b are positioned in a triangular arrangement, in which they are in close proximity to one another. Such an arrangement facilitates operation of syringe 10 with a single hand of an individual (e.g., the index finger, thumb, and middle finger of one hand, as previously described). By allowing an individual to operate syringe 10 and, thus, to perform any procedure in which fluid pressure is directly or indirectly applied to any human body part, including a spinal disk or an artery, with a single hand, the individual is free to use his or her other hand to accomplish additional tasks, particularly those associated with the procedure being performed.

The Plunger

Figure 3:
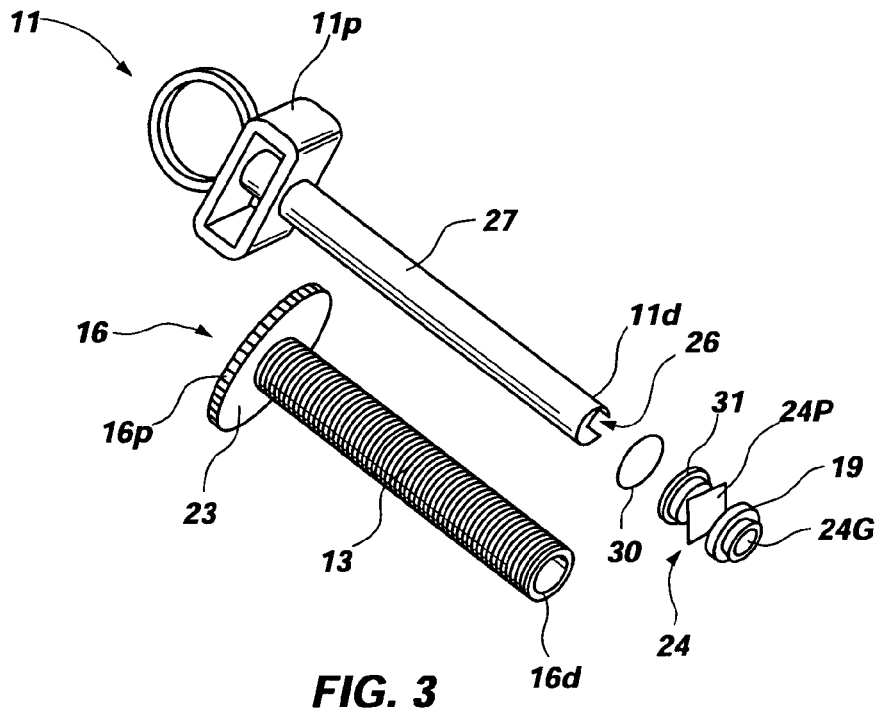
FIG. 3 is an exploded view of a plunger of the syringe and a rotatable sleeve that encases the plunger.

With reference to FIG. 3, the majority of plunger 11 is an elongate, at least partially hollow element, which has an outer surface 27 and includes an inner bore 26 that is located for communication with a distal end 11d of plunger 11. Additionally, plunger 11 may include a somewhat annular end cap 19 at distal end 11d thereof, which is configured to retain a pressure transducer 24 and transducer retainer 31 in place relative to inner bore 26, while allowing for the communication of fluid pressure from the exterior (at least at distal end 11d) of plunger 11 to pressure transducer 24.

Pressure transducer 24 may comprise any transducer or group of transducers that is suitable for accurately measuring fluid pressures within one or more ranges that may be encountered by use of syringe 10. Exemplary transducers that may be employed as pressure transducer 24 include those described in the aforementioned Wallace patents, the disclosure of each of which is hereby incorporated herein in its entirety by this reference.

A quantity of gel 24G of a type known in the art (e.g., a silicone gel) may also be disposed within an aperture 19A of end cap 19 and over a pressure-sensing region 24P of pressure transducer 24 to provide some protection thereto. Of course, gel 24G is of a type that accurately transmits fluid pressure present at distal end 11d of plunger 11 to pressure-sensing region 24P and may, therefore, also be referred to as a "force transmitting gel."

Transducer retainer 31 is a small, somewhat annular element. Transducer retainer 31 is configured to be securely positioned relative to inner bore 26 and end cap 19. Features of transducer retainer 31 are configured to be secured to pressure transducer 24. Transducer retainer remains in a fixed position within inner bore 26 and, along with end cap 19, fixes pressure transducer 24 in position along plunger 11 during movement of plunger 11 and when high fluid pressures are present within the lumen of barrel 14 (FIG. 1).

Figure 4A:
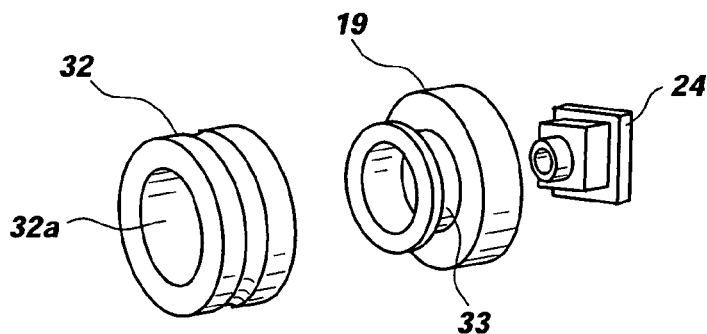
FIGS. 4A and 4B are exploded views of components associated with the distal end of the plunger.
Figure 4B:
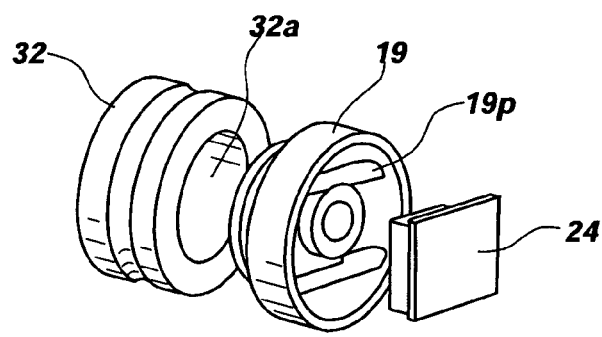

As shown in FIGS. 4A and 4B, end cap 19 includes a detent 33 at a distal end 19d thereof. Detent 33 is configured to receive corresponding features on the interior of a rubber plunger tip 32, which seals against an inner surface of barrel 14. As depicted, plunger tip 32 includes an aperture 32a therethrough to facilitate the communication of fluid pressure to pressure transducer 24.

Figure 5:
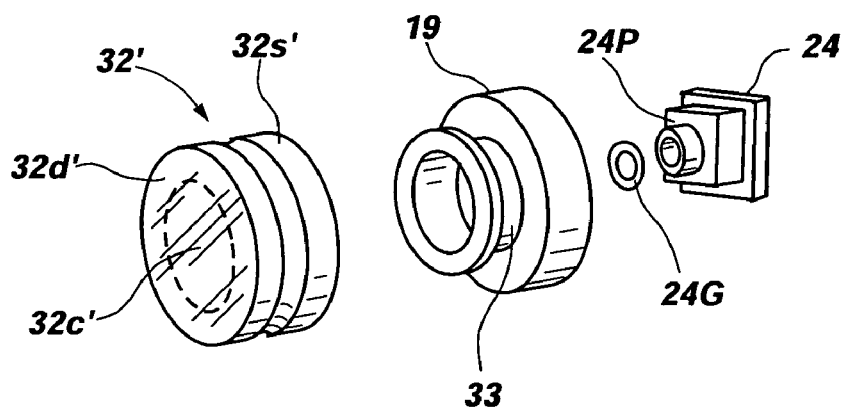
FIG. 5 is an exploded view that includes a perspective view of a tip that is associated with the distal end of the plunger to shield a pressure transducer of the syringe while accurately transmitting fluid pressure to the pressure transducer.

Alternatively, with reference to FIG. 5, a plunger tip 32' that covers a pressure-sensing region 24P of pressure transducer 24 may be positioned over distal end 11d of plunger 11 (FIG. 3), such as over the illustrated end cap 19 that is to be secured to distal end 11d. Plunger tip 32' includes a somewhat rigid sealing element 32S' at the outer periphery thereof, which surrounds a central element 32C'.

Rigid sealing element 32S' of plunger tip 32' is configured to be secured to an end of plunger 11. Without limiting the scope of the invention, rigid sealing element 32S' may be configured to be secured to end cap 19, as illustrated. Accordingly, rigid sealing element 32S' may include an internally protruding ridge (not shown) that is configured to be inserted into and engaged by detent 33 of end cap 19. Additionally, rigid sealing element 32S' of plunger tip 32' is configured to seal against an inner surface of barrel 14 (FIG. 1).

Central element 32C' of plunger tip 32' is configured to be disposed over, to substantially shield, and to accurately transmit fluid pressure to pressure-sensing region 24P of pressure transducer 24 and, optionally, gel 24G located thereover. In the illustrated example, central element 32C' is disposed over an aperture 19A of end cap 19, through which fluid pressure is communicated to pressure-sensing region 24P. Central element 32C' may comprise the majority of a distal surface 32d' of plunger tip 32' (e.g., about 60% to about 70% of the area of distal surface 32d'). By way of example only, central element 32C' may be a pliable element that substantially shields pressure transducer 24 from fluids that are present at distal end 1d of plunger 11 (FIG. 3). The thickness of such an embodiment of central element 32C' and the material (e.g., silicone) from which such a central element 32' is formed are together configured to accurately transmit fluid pressure that is present at distal end 1d of plunger 11 to pressure-sensing region 24P of pressure transducer 24.

Other arrangements for securing a pressure transducer 24 to a plunger of a syringe may also be utilized and, thus, are also within the scope of the present invention.

Electronics

Figure 7:
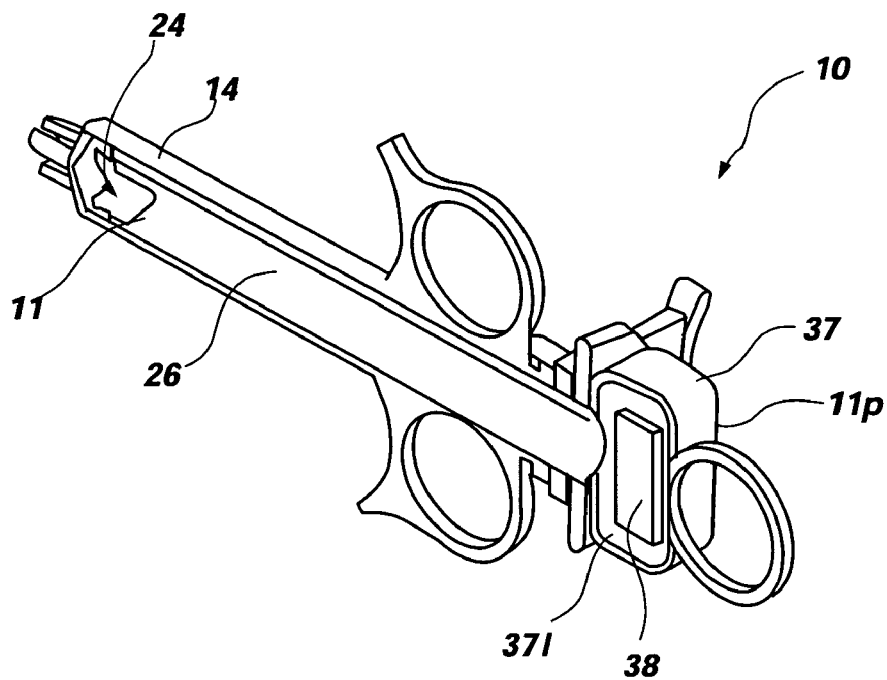
FIG. 7 is a cross-sectional perspective view of the syringe of FIG. 1.

Turning to FIG. 7, which is a perspective, sectional view of syringe 10 taken along the central longitudinal axis of plunger 11 and barrel 14 thereof, inner bore 26 may extend along substantially the entire length of plunger 11. Additionally, plunger 11 may include an enlarged, hollow region 37 at proximal end 11p thereof with an interior 37I that communicates with inner bore 26. It is within interior 37I that an electronics assembly 38 may be incorporated to connect pressure transducer 24 to a display element 39 (FIGS. 8A through 8C), which may be located at proximal end 11p of plunger 11.

Wires (not shown) may extend through inner bore 26 to connect pressure transducer 24 with corresponding elements of the electronics assembly, as known in the art. Alternatively, inner bore 26 may facilitate wireless communication between pressure transducers and corresponding elements of the electronics assembly, as described in further detail hereinafter.

Figure 7A:
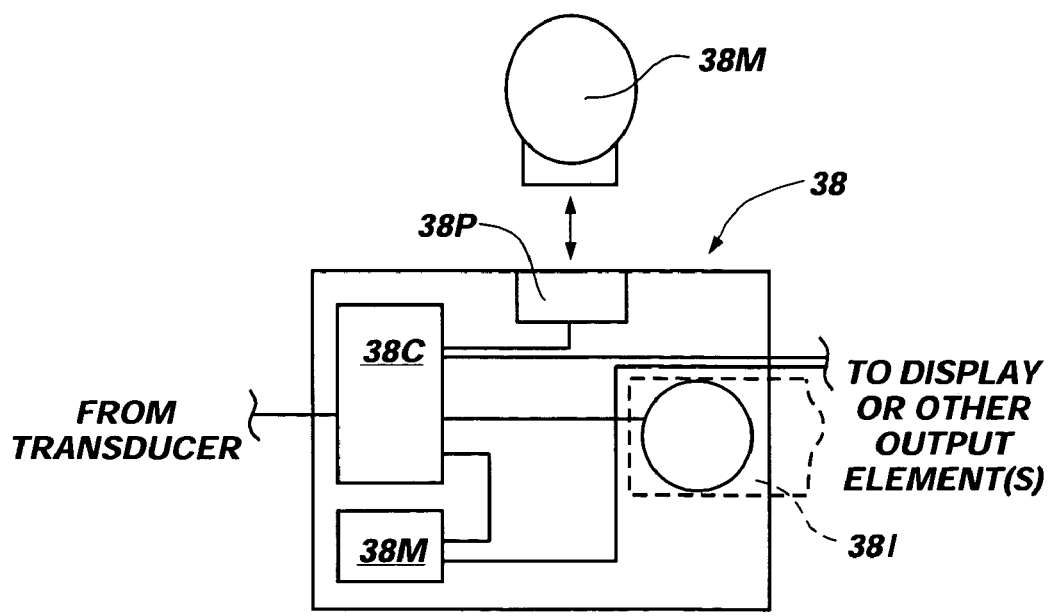
FIG. 7A is a schematic representation of exemplary electronics that may be associated with a syringe according to the present invention.

Electronics assembly 38 may, as shown in FIG. 7A, include one or more microcontrollers 38C or other processing elements of a type known in the art, which receive signals from pressure transducer 24, process the received signals, then output a signal that causes display element 39 to display a numeric indicator of the pressure that has been sensed at distal end 11d of plunger 11 by pressure transducer 24. Electronics assembly 38 also includes a power source 38B, such as a battery, which may have a voltage (e.g., 3 V) sufficient for operating microcontroller 38C, display element 39, and other elements that are part of or otherwise associated with electronics assembly 38.

Communication between power source 38B and other electronic elements may be controlled by a switch of a known type. Alternatively, a power inhibitor 38I, which is formed from electrically insulative material (e.g., plastic, paper, plastic-coated paper, ceramic, glass, etc.) may be positioned between power source 38B and a contact (not shown) to power source 38B. When power inhibitor 38I is removed, electrical communication between power source 38B and the contact and, thus, electronic components of syringe 10 (FIG. 7) in communication with the contact is established.

Each time power is initially provided to microcontroller 38C, such as when power is initially provided to microcontroller 38C, microcontroller 38C may be programmed to enter a "zero loop." In the "zero loop," microcontroller 38C determines whether less than a minimum threshold or more than a maximum threshold in differential pressure (e.g., relative to atmospheric pressure, which is equal to zero) is being measured by pressure transducer 24 (FIG. 7). As an example, and not to limit the scope of the present invention, the maximum threshold may be set at about 4 to about 4½ psi, which accommodates the typically 2½ psi variation between atmospheric high and low pressures, as well as variations in pressure at different elevations. Such programming of microcontroller 38C may permit microcontroller 38C to receive pressure signals from pressure transducer 24 for a given period of time (e.g., ten seconds), to provide a more accurate sample of the measured pressure. If the fluid pressure that has been measured by pressure transducer 24 exceeds the maximum threshold, microcontroller 38C shuts down, causes display element 39 to shut down, or go "dark" or "blank," and restarts, automatically reentering the "zero loop." When the fluid pressure that is initially measured following provision of power to microcontroller 38C is at or below the maximum threshold, microcontroller 38C may output some indication that pressure transducer 24 has been calibrated, such as by causing display element 39 to show the characters "CAL." Programming of this type prevents inaccurate pressure measurements that may be caused accidentally or by misuse of syringe 10 and provide a user of syringe 10 with an indication of the existence of a problem.

An improper initial pressure may be caused by a variety of factors, including, without limitation, if gel 24G (FIG. 5)

sticks to an adjacent area of plunger tip 32 (FIGS. 4A and 4B) (which may result in a lower-than-actual) pressure reading by pressure transducer 24), leaving a cap over connection element 20 (FIG. 1) of barrel 14 (FIG. 3), the presence of bubbles in a fluid within the lumen of barrel 14, a premature build-up of pressure within barrel 14 (e.g., by using syringe 10 before power is provided to microcontroller 38C), or otherwise. In reaction to the repeated initialization and shutting down of microcontroller 38C as a result of the detection of an undesirable fluid pressure as a "zero loop" is being effected, a user may be prompted to evaluate syringe 10 and its various components and correct the problem, then restart microcontroller 38C.

The display element 39 (FIGS. 8A and 8B) of syringe 10 (FIG. 7) that communicates with microcontroller 38C may comprise any suitable type of display known in the art. By way of nonlimiting example, display element 39 may comprise one or more groups of light emitting diodes (LEDs), each of which may be illuminated in a variety of combinations to form a corresponding variety of characters (e.g., numbers, letters, etc.). As another example, display element 39 may comprise a liquid crystal display of a known type, which likewise includes elements that may be stimulated into displaying combinations of lines that form a variety of different characters. Of course, any other type of display that would be suitable for displaying pressure information and any other desired information that has been processed and output by microcontroller 38C (e.g., in the form of characters, images, etc.) may also be used in a syringe 10 of the present invention without departing from the scope of the present invention.

In addition to processing pressure signals that have been received from pressure transducer 24 (FIG. 7), a microcontroller 38C of electronics assembly 38 that incorporates teachings of the present invention may be programmed to cause any displayed characters to flash when it may be desirable to catch the attention of an individual who is operating syringe 10. Alternatively or additionally, microcontroller 38C may transmit signals to other output elements (not shown), such as audio outputs, vibratory outputs, or the like, to provide a caution or warning to an individual who is using syringe 10. Such signals may be provided merely for information purposes, or for safety purposes. For example, if the fluid pressure measured at distal end 11d of plunger 11 by pressure transducer 24 exceeds a threshold value (e.g., 125 psi, which is approaching the upper limit of pressure that should be encountered during discography), microcontroller 38C may cause characters of display element 39 (or images or a backlight on any other type of display element), which may show a value representative of the measured pressure, to repeatedly flash.

In some embodiments of syringe 10, electronics assembly 38 may include a memory element 38M in communication with microprocessor 38C. Memory element 38M may, by way of example only, comprise a flash-type memory (i.e., flash EEPROM) associated with microprocessor 38C. Such a memory element 38M may be an internal element, which is permanently associated with microprocessor 38C, or an external element, which is configured to temporarily communicate with microprocessor 38C by way of a communication element 38P (e.g., a USB port), then be removed therefrom and used elsewhere. Of course, communication elements 38P that communicate with microcontroller 38C may also be used for any other suitable purpose, including for establishing communication between microcontroller 38C and a processing element (e.g., a processor) of a computer (e.g., for further evaluation of transmitted data, to transfer data from memory element 38M for storage on a centrally accessible file, etc.).

Internal memory elements 38M may be used with syringes 10 that include reusable electronics assemblies 38. External memory elements 38M are particularly useful when transfer of the data stored thereon is desirable, or when syringe 10, including electronics assembly 38 and display element 39 thereof, is disposable.

A further embodiment of syringe according to the invention incorporates a wireless transmission of pressure information from the pressure transducer to the read-out display at the proximal end of the syringe. The transducer analog output may be introduced to a wireless transmitter to transmit an analog signal to the distal end of the syringe, where a wireless receiver receives the signal, and converts it to a digital signal, which is introduced directly into the digital read-out display.

The wireless transmitter may be an infrared processor/transmitter which receives the analog electrical signal, converts it into an infrared analog signal which is emitted from an infrared (IR) emitter, which has a battery associated therewith. The IR analog signal may be transmitted through the body of the syringe through an open channel to an IR analog receiver/converter at the proximal end of the syringe. Alternatively, the electrical signal may be converted into a digital IR or other digital wireless signal to be received by an appropriate receiver. An optical fiber may be advantageously used for precise IR transmission from the IR transmitter to the IR receiver. Further, a digital signal may be sent via an electrical conductor between the transducer/transmitter and the receiver/display.

The IR signal may include pulses that flash at a rate which is indicative of a particular pressure measurement by pressure transducer 24 (FIGS. 3 through 5), or that are embedded with data and, thus, pulse in a manner that is indicative of the embedded data (e.g., somewhat like Morse Code).

The disclosure of U.S. Pat. Nos. 5,215,523 and 5,387,194 to Williams/Call et al., the disclosures of both of which are hereby incorporated herein in their entireties by this reference, especially with respect to means and systems for wireless transmission of signals produced by a pressure transducer. Also, incorporated herein is U.S. Pat. No. 5,021,046 to Wallace, especially the disclosure relating to pressure transducers.

Also, wireless transmission of pressure transducer information by radio signals may be utilized within the syringe for the purposes of the invention. However, radio signals may interfere with various other equipment in an operating room-type of environment and would generally be contraindicated where such a syringe was to be utilized upon a patient having a pacemaker.

Figure 8A:
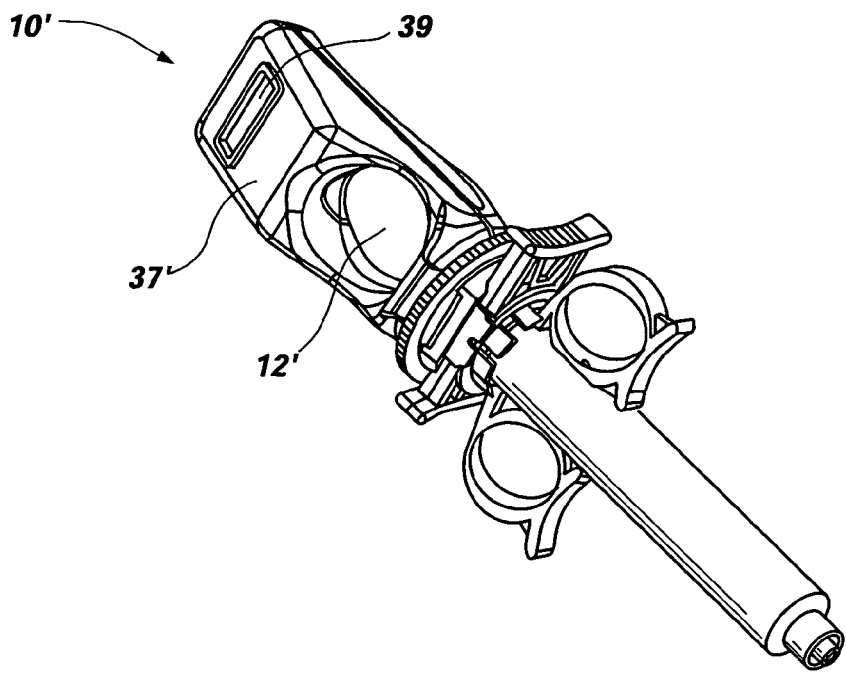
FIGS. 8A-8C are perspective views of a syringe with a streamlined block-shaped head containing a display element of a syringe that incorporates teachings of the present invention.
Figure 8B:
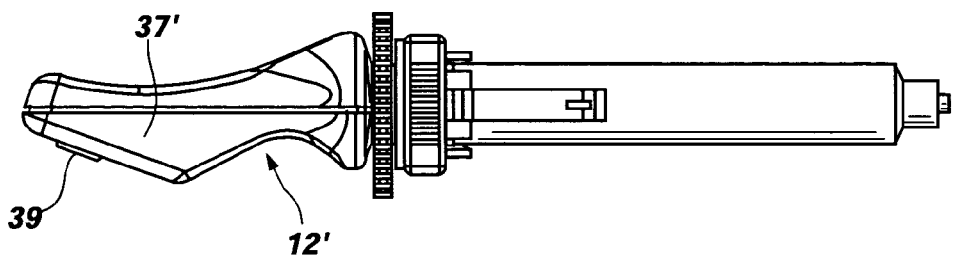
Figure 8C:
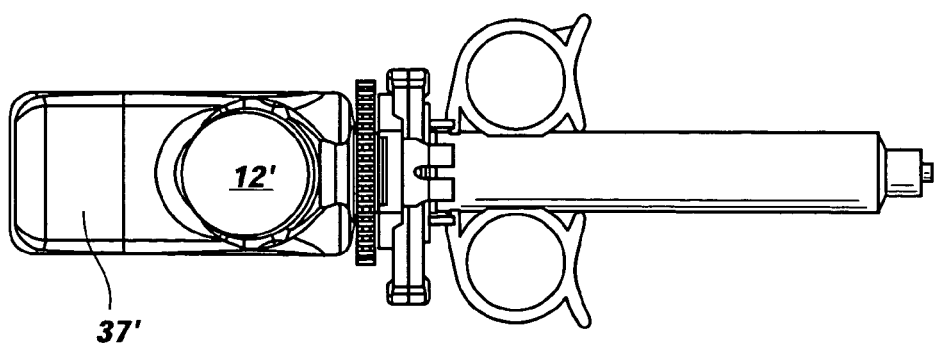

FIGS. 8A through 8C are perspective views of a syringe with a pressure display head located in a display holder having a thumb aperture located between the display and the plunger.

FIG. 8A is a perspective view of a syringe 10' with a pressure display element 39 located in a display holder 37' having a thumb aperture 12' located between the display and the plunger. Syringe 10' may include a wired connection between the pressure transducer and the pressure display or a wireless transmission system such as that illustrated in FIG. 9.

FIG. 8B and 8C show an elevational view and plan view, respectively, of syringe 10' (i.e., an infuser) of FIG. 8A. The display holder 37' of syringe 10' is unique in appearance, as can be seen in FIGS. 8A, 8B and 8C. Additionally, the style, shape and juxtaposition of the various elements of the syringe further provide a syringe 10' of a distinctive appearance.

FIG. 8C shows the bottom of the display holder 37', assuming that the surface in which the display is embedded is denoted the top surface, which is visible in FIGS. 8A and 8B.

The syringe 10' of FIGS. 8A, 8B, and 8C has the thumb preferably inserted in thumb aperture 12' from the bottom so that the display element 39 will face upwards to the technician operating syringe 10'.

Figure 9:
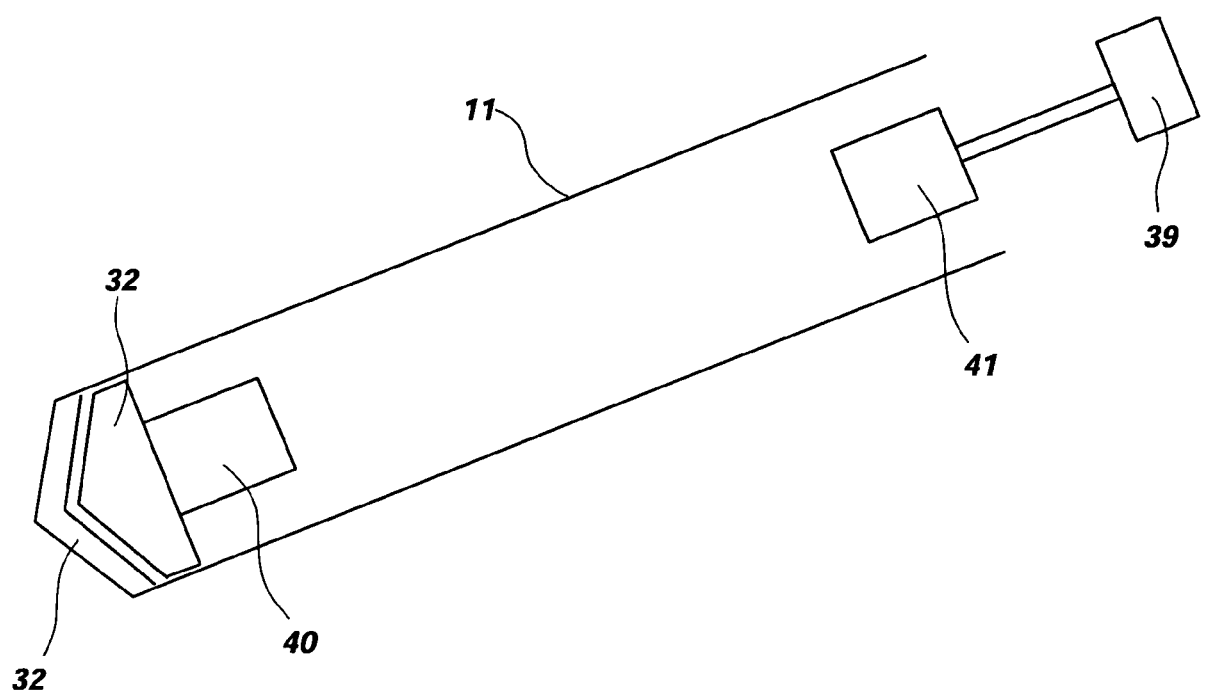
FIG. 9 is a cross-sectional view of a plunger having electronics that transmit a wireless signal to a display element located at a proximal end of the plunger.

An embodiment of the invention is shown in FIG. 9 illustrating in perspective view a hollow plunger 11 having a pressure transducer 24 located at or near plunger tip 32 (distal end), which transducer is electrically connected to an electronics system 40 which wirelessly transmits its output signal (IR or radio frequency (RF)) to a remote receiver/pressure display 41 system. Display element 39 may be located at or near the proximal end of plunger 11 or at a remote location separate from plunger 11, e.g., attached to an external surface of The syringe or entirely separate and remote from the syringe, e.g., on a support which positions the pressure display element 39 visible to one or more members of a team involved in an infusion procedure.

The signal transmitted from the electronics system to the display may be an analog or digital signal. If the signal is an analog signal then the pressure display includes a receiver mechanism which receives the signal and converts the analog signal to a digital signal suitable for being displayed as a pressure in millimeters of mercury, pounds per square inch or other useful pressure units. The electronics may further include a memory device whereby the total infusion procedure is recorded in terms of elapsed time and regular (substantially continuously, if desired) pressure recordings so that a history of the entire infusion procedure may be later downloaded for permanent storage.

A substantially hollow plunger having an internal pressure sensing mechanism, e.g., pressure transducer, in the tip which is in direct or indirect contact with fluid of a syringe being pressurized has many advantages, many of which have been enumerated herein. One such advantage is that a direct pressure reading may be displayed in a display incorporated in the proximal end of the plunger. Also, in a structure such as described herein, a fluid, preferably liquid, may be contained within the hollow plunger to contact a dynamic (diaphragm) type-pressure influenced mechanism and conduct the received pressure through said fluid, preferably liquid, to a pressure transducer/display in the proximal end of the plunger.

In such a structure the pressure experienced at the tip of the plunger is transmitted by a fluid conductor to a pressure transducer or other pressure metering means, e.g., an analog pressure meter, at the proximal end of the plunger. Such a structure permits all the electronics necessary for a digital display, e.g., pressure transducer, analog/digital converter and digital signal receiving display to be directly coupled to one another and located at or near the proximal end of the hollow plunger.

Figure 10:
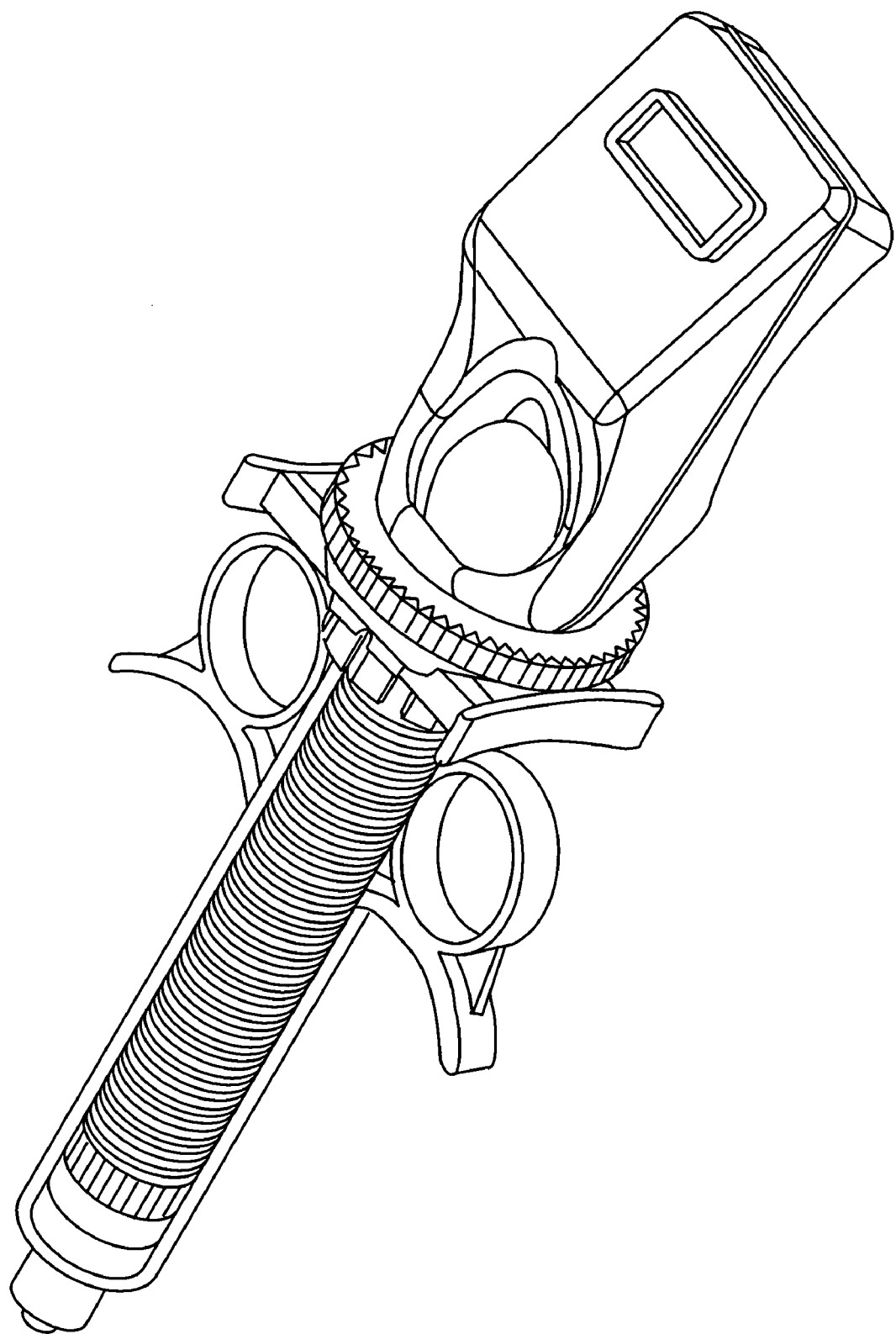
FIG. 10 is a perspective view of the syringe of FIGS. 8A-8C with a fanciful display holder.

The display at the proximal end of the syringe may be incorporated into a housing of the varying shapes and designs shown herein which accommodate functional purposes. The shape of the display housing shown in FIGS. 8A through 8C may be somewhat fanciful to provide a smooth aesthetic appearance while not diminishing its attributes as a display holder and thumb engagement device. A further perspective view of the syringe of FIGS. 8A through 8C is shown in FIG. 10. The view is at an oblique angle from the rear of the syringe.

Figure 11:
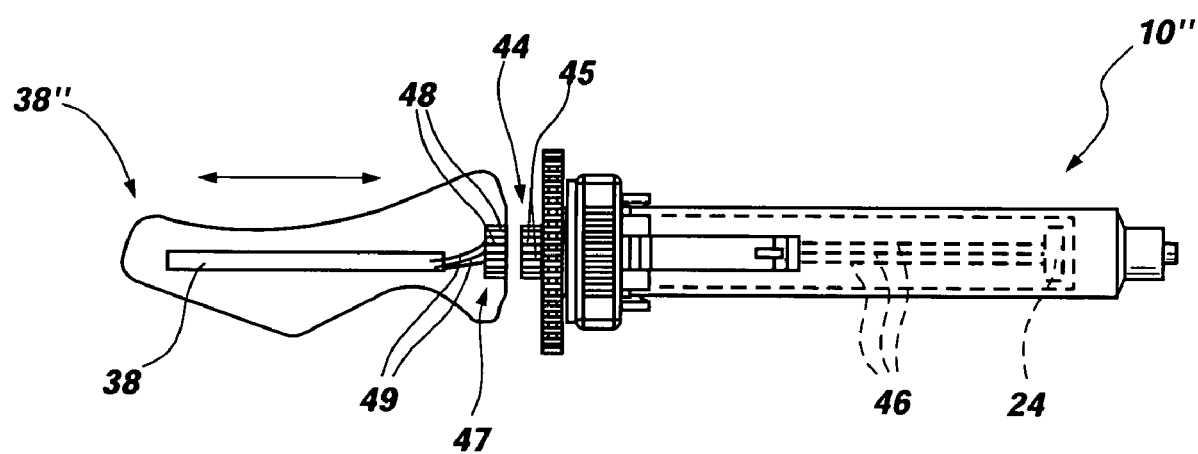
FIG. 11 is an exploded view of a plunger that includes a reusable electronics and display module which is detachable from the remainder of the syringe.

FIG. 11 illustrates another embodiment of syringe 10" according to the present invention, which includes wires 46 that extend from the pressure transducer 24 thereof. Modular electronics 38" may be "plugged into" and "unplugged" from an electrical connector 44, or plug, of known type of syringe 10". Electrical connector 44 may be positioned adjacent to distal end 11d of plunger 11 in a relatively fixed position.

Electrical connector 44 includes pins or receptacles 45 that communicate with one or more wires 46. Wires 46, in turn, communicate with corresponding contacts (not shown) of a pressure transducer 24.

Modular electronics 38" also include an electrical connector 47, which is configured complementarily to electrical connector 44 and, thus, includes receptacles or pins 48 that are positioned and configured to cooperate and electrically communicate with corresponding pins or receptacles 45 of electrical connector 44. Receptacles or pins 48 have wires 49 coupled thereto, which establish communication with one or more of components (e.g., microcontroller 38C, power source 38B, etc.) of an electronic assembly 38 of modular electronics, such as the exemplary electronic assembly 38 depicted in FIG. 7A.

By way of example only, electrical connectors 44 and 47 may comprise electronic (e.g., computer) communication ports of known type that are configured to mate with one another.

As modular electronics 38" may be uncoupled from syringe 10", modular electronics 38" may be used repeatedly, with a plurality of disposable syringes 10". Additionally, modular electronics 38" may be coupled with a communication port of a computer or other electronic device to facilitate programming of one or more elements (e.g., microcontroller 38C) of electronic assembly 38, data transfer (e.g., from memory element 38M of electronic assembly 38), or for any other reason to establish communication between one or more components of electronic assembly 38 and an external electronic device.

Elements for Positioning the Plunger

Figure 2:
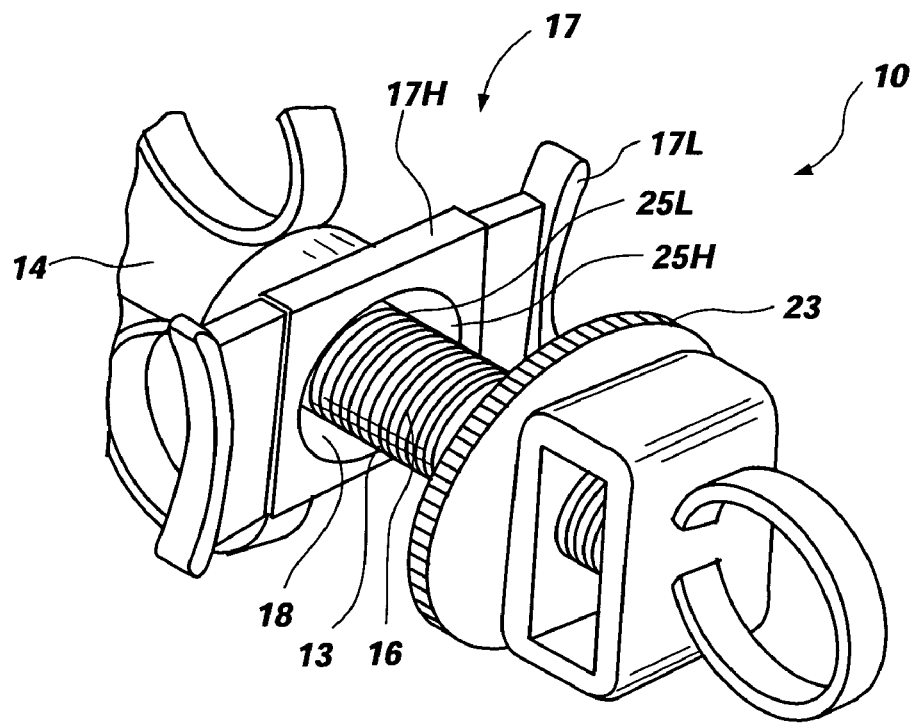
FIG. 2 is a perspective view of the proximal portion of the syringe of FIG. 1.

With returned reference to FIGS. 1 through 3, syringe 10 may additionally include means for adjusting the position of plunger 11 within barrel and, thus, for controlling the amount of pressure generated by syringe 10. The means for adjusting may be configured to provide for fine adjustments of the position of plunger 11 and, thus, of the pressure generated by syringe 10, as well as for larger adjustments.

Fine adjustments of the position of plunger 11 within barrel 14 may, for example, be accomplished with the depicted rotatable sleeve 16, which is an elongate, hollow, cylindrical element that is disposed, as a sleeve, over and may be supported by at least a portion (e.g., a smooth portion) of outer surface 27 of plunger 11. After rotatable sleeve 16 is slid over plunger 11, a friction reduction washer 30 may be placed over outer surface 27 of plunger 11, adjacent to distal end 16d of rotatable sleeve 16, to act as a friction reducing bearing between rotatable sleeve 16 and end cap 19 and, thus, to facilitate the substantially free rotation of rotatable sleeve 16 relative to end cap 19. Rotatable sleeve 16 includes threads 13 on an exterior surface thereof and a control element 23, such as the depicted wheel, at a proximal end 16p thereof.

Threads 13 may be engaged by corresponding features (not shown) of a locking mechanism 17, which is associated with and remains in a substantially fixed location relative to proximal end 14p of barrel 14. Locking mechanism 17 includes a housing 17H and a locking element 17L. Apertures 25H and 25L of housing 17H and locking element 17L, respectively, accommodate rotatable sleeve 16. Housing 17H is secured in place relative to proximal end 14p of barrel 14 (e.g., by being molded integrally therewith, bonded thereto, etc.). Locking element 17L is associated with housing 17H and may be moved relative thereto.

As shown in FIG. 2, housing 17H is configured to captivate locking element 17L in such a way that locking element 17L may slide laterally relative to housing 17H and radially relative to barrel 14. In the illustrated example, opposite ends of locking element 17L are exposed through housing 17H to facilitate movement thereof. Aperture 25H of housing 17H has dimensions that facilitate the substantially free longitudinal movement of rotatable sleeve 16 and, thus, the plunger 11 therein transversely thereto. Aperture 25L of locking element 17L may comprise a keyhole-shaped opening, which may include two overlapping circular apertures, one having a larger diameter than the other. The smaller side of aperture 25L has dimensions that facilitate engagement of threads 13 of rotatable sleeve 16, while the dimensions of larger side of aperture 25L are configured not to engage threads 13 and, thus, allow substantially free travel of plunger 11 longitudinally through barrel 14.

Locking element 17L may be placed in a locked, or set, position by causing an interior rib 18, which is located at an edge of the smaller side of aperture 25L, to engage threads 13 of rotatable sleeve 16 (e.g., by insertion within a groove of threads 13). When in an unlocked, or released, position, interior rib 18 disengages threads 13 of rotatable sleeve 16, permitting substantially longitudinal movement of rotatable sleeve 16 and, thus, plunger 11 through barrel 14.

When locking mechanism 17 is in a locked position (e.g., slid to one side), fine, or minute, adjustments of the position of plunger 11 within barrel 14 and, thus, associated fine or minute adjustments to volume or pressure within the lumen of barrel 14 may be made by use of control element 23. For example, if control element 23 comprises a wheel which is positioned and configured to be rotated by the thumb of an individual (and, thus, may also be referred to herein as a "thumbwheel"), displacement of plunger 11 relative to barrel 14 may be generated by rotation of control element 23. Rotation of control element 23 in a direction that forces rotatable sleeve 16 against a flange, such as that provided by a proximal edge 19p (FIG. 4B) of end cap 19, against which distal end 16d of rotatable sleeve abuts, thereby forcing plunger 11 distally along the length of barrel 14. As fluid pressure within the lumen of barrel 14 may exert force on plunger 11, rotation of control element 23 and, thus, rotatable sleeve 16 in the opposite direction (i.e., such that rotatable sleeve 16 moves proximally relative to barrel 14), plunger 11 may move proximally relative to barrel 14. The axial advancement or retraction of plunger 11 effected by rotation of control element 23 is very slight, thus, minute adjustments of fluid pressure are readily accomplished. The ability to achieve such precise adjustment of fluid pressure is desirable in a number of medical procedures, including, but not limited to, discography and angioplasty procedures.

When locking mechanism 17 is in an unlocked position (e.g., slid to the other side), plunger 11 may be substantially freely moved along the length of barrel 14 by placing force on proximal end 11p thereof (e.g., as an individual places his or her thumb within the depicted grasping element 12, then moves his or her thumb). Thus, larger adjustments of the position of plunger 11 may be made when locking mechanism 17 is in an unlocked position.

When fluid pressure within the lumen of barrel 14 increases, positioning of locking mechanism 17 in an unlocked position, so as to release threads 13, allows the fluid pressure to force plunger 11 proximally through barrel 14, facilitating a rapid, substantially instantaneous reduction of pressure (e.g., to zero additional pressure exerted by syringe 10) within barrel 14 and, thus, within a portion of the body of a subject with which the lumen of the barrel 14 is in fluid communication. This feature is desirable since many procedures may require a substantially instantaneous release of fluid pressure to prevent or minimize damage to a body part that is being treated or investigated.

Figure 6A:
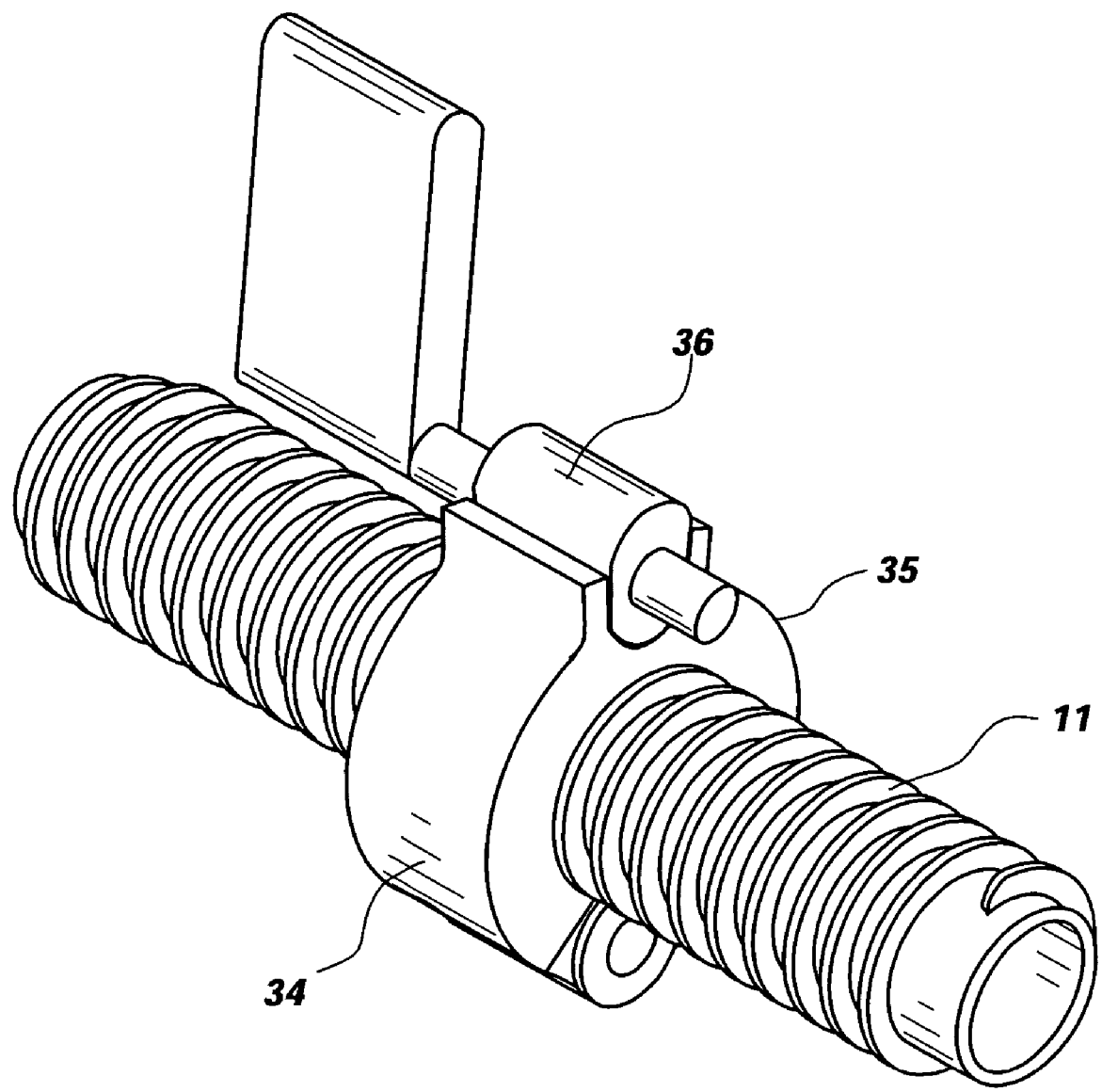
FIGS. 6A-6C include several views of a clamshell locking mechanism for a syringe of the present invention.
Figure 6B:
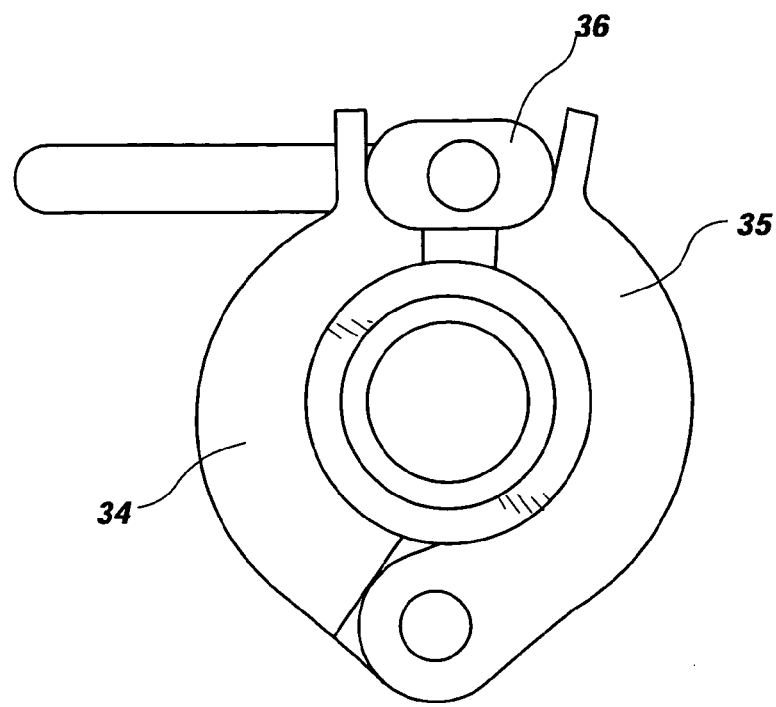
Figure 6C:
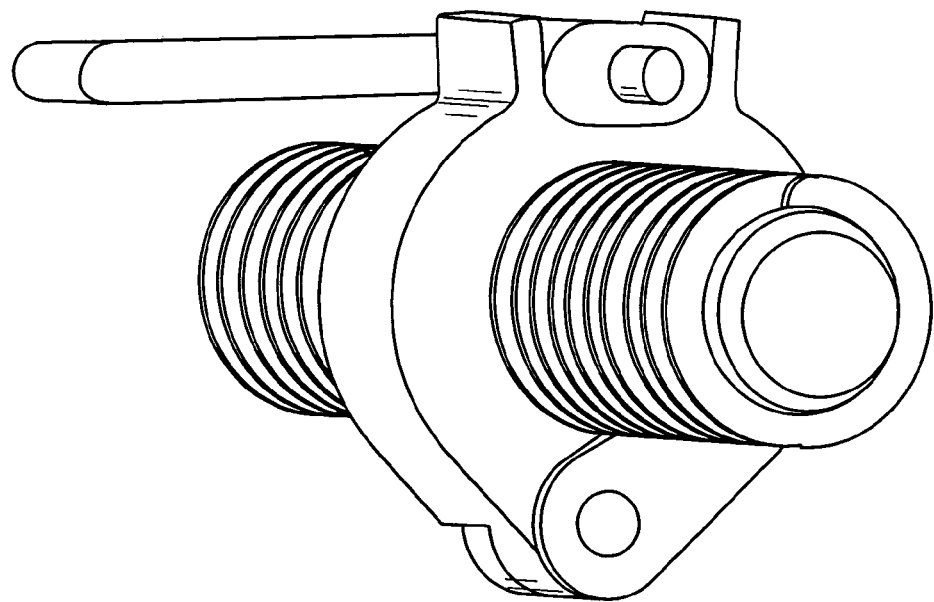

While a particular embodiment of slide-lock mechanism has been illustrated and described herein, other locking mechanisms may be also effectively utilized on syringes that incorporate teachings of the present invention. For example, a two-piece clam-shell, spring-loaded mechanism, such as that shown in FIGS. 6A through 6C, can be usefully employed. Two clam-shaped elements 34 and 35 are hinged at their closed ends and spring-biased to be in a "closed" position, as shown in FIG. 6A. A rotatable cam 36, which has an elongate cross-section taken transversely to the length thereof, is positioned between clam-shaped elements 34 and 35, at the open ends thereof. While the smaller dimension of rotatable cam 36 separates clam-shaped elements 34 and 35, they remain in the "closed" position. When the rotatable cam is rotated, larger dimensions thereof separate the open ends of clam-shaped elements 34 and 35, forcing them apart from one another and into an "open" position, as shown in FIGS. 6B and 6C. When clam-shaped elements are in the "open" position, a threaded rotatable sleeve 16 or a threaded plunger 11' may slide freely therebetween.

Alternative mechanisms for locking and unlocking threaded rotatable sleeve 16 (FIGS. 1 through 3) or a threaded plunger (FIGS. 6A through 6C) in a fixed position to provide minute pressure adjustment may be also employed without departing from the scope of the present invention, including, without limitation, the locking mechanisms that are disclosed in U.S. Pat. Nos. 5,860,955, 5,433,707, and 5,685,848, the disclosures of which are hereby incorporated herein in their entireties by this reference.

Having a rotatable sleeve 16 that may be engaged or disengaged by a locking mechanism (e.g., locking mechanism 17 (FIGS. 1 and 2) or locking mechanism 17' (FIGS. 6A through 6C)) permits minor axial adjustments of plunger 11 without requiring that plunger 11 itself be rotated. Thus, any features of syringe 10, such as display element 39 (FIGS. 8A through 8C), that are affixed at proximal end 11p of plunger 11 remain in a constant position (and, in the case of display element 39, in a continuously visible position).

If, however, pressure transducer 24 (FIGS. 3 through 5) and its associated electronics (not shown) are integrated into a plunger, with the electronics being configured to transmit wireless signals to remote processing or display apparatus, then the plunger 11' (FIGS. 6A through 6C) itself may be threaded, at least near its proximal end 11p, for engagement with a suitable locking mechanism (e.g., locking mechanism 17 (FIGS. 1 and 2) or locking mechanism 17' (FIGS. 6A through 6C)) and, thus, rotated to accomplish minute axial adjustment of the position of plunger 11 along the length of barrel 14. The grasping element 12 associated with such a plunger 11 may be configured (e.g., a ring with an enlarged open diameter) to facilitate operation of plunger 11 with an individual's thumb regardless of slightly offset rotation of grasping element 12.

Syringes 10 that include grasping elements 12 (e.g., a ring), electronics, and/or display element 39 (and, of course, wireless connections or rotatable connection elements) that are secured in position relative to proximal end 11p of plunger 11 in such a way that they substantially freely rotate relative to proximal end 11p are also within the scope of the present invention.

Referring again to FIG. 1, it is currently preferred that an individual who uses syringe 10 be able to control the position (i.e., locked or unlocked) of locking mechanism 17 with the same hand that he or she is using to hold or operate other features of syringe 10. For example, the individual may use his or her thumb to set (i.e., lock) or release (i.e., unlock) locking mechanism 17, while holding grasping elements 15a and 15b with the index finger and middle finger of the same hand. The location of control element 23 vis-a-vis grasping elements 12, 15a, and 15b may likewise readily permit an individual using syringe 10 to remove his or her thumb from grasping element 12 and place it upon control element 23 to rotate control element 23 to achieve minute fluid pressure adjustments, further facilitating continuous one-handed operation of syringe 10.

Use of a syringe 10 that incorporates teachings of the present invention facilitates control over the pressure generated or measured thereby with a single hand, while the individual operating syringe 10 may use his or her other hand to perform other tasks. For example, in discography procedures, the individual's free hand may be used to position a stylus that communicates with syringe 10, while the hand that holds syringe 10 is used to inject additional fluorescent media to provide additional illumination on a fluoroscope and, thus, a better idea of the actual location of an end of the stylus.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A syringe comprising:
a barrel;
a plunger positionable within and translatable along a length of the barrel;
a pressure transducer housed at least partially within an interior of the plunger;
a longitudinal adjustment mechanism configured to selectively provide ingress and retraction of said plunger;
a threaded adjustment mechanism configured to selectively provide ingress and retraction of said plunger; and
a locking mechanism having a first position and a second position, wherein said first position disengages at least one thread of said locking mechanism to enable use of said longitudinal adjustment mechanism, and wherein said second position engages said at least one thread of said locking mechanism to enable use of said threaded adjustment mechanism.

2. The syringe of claim 1, wherein the plunger includes a tip having an aperture corresponding with said pressure transducer to enable communication of fluid pressure to said pressure transducer.

3. The syringe of claim 2, further comprising a quantity of gel disposed within at least a portion of said aperture.

4. The syringe of claim 3, wherein the pressure transducer is located near a distal end of said plunger.

5. The syringe of claim 2, wherein said tip comprises:
an outer periphery configured to engage an end of the plunger; and
a central region configured to transmit fluid pressure to the pressure transducer.

6. The syringe of claim 5, wherein the central region comprises a thin, pliable element.

7. A syringe comprising:
a barrel;
a plunger positionable within and translatable along a length of the barrel, said plunger comprising a pressure transducer;
a longitudinal adjustment mechanism configured to selectively provide ingress and retraction of said plunger;
a threaded adjustment mechanism configured to selectively provide ingress and retraction of said plunger;
a locking mechanism having a first position and a second position, wherein said first position enables use of said longitudinal adjustment mechanism and prevents use of said threaded adjustment mechanism, and wherein said second position enables use of said threaded adjustment mechanism and prevents use of said longitudinal adjustment mechanism;
an electronic assembly in communication with the pressure transducer and including a communication element; and
a removable memory element configured for temporary connection with the communication element.

8. The syringe of claim 7, wherein the communication element comprises a USB port.

9. The syringe of claim 7, wherein the removable memory element comprises flash memory.

10. A method for transporting data from a pressure-sensing system of a syringe to a processing element external to the pressure-sensing system, the method comprising:
providing a syringe having a barrel, a plunger, a pressure transducer, a longitudinal adjustment mechanism, a threaded adjustment mechanism, and a locking mechanism, wherein said plunger comprises said pressure transducer and is positionable within and translatable along a length of said barrel, wherein said longitudinal adjustment mechanism is configured to selectively provide ingress and retraction of said plunger, and wherein said threaded adjustment mechanism is configured to selectively provide ingress and retraction of said plunger, and wherein said locking mechanism comprises a first position and a second position, said first position enabling use of said longitudinal adjustment mechanism and preventing use of said threaded adjustment mechanism, and said second position enabling use of said threaded adjustment mechanism and preventing use of said longitudinal adjustment mechanism;
using said syringe to obtain pressure-sensing information;
establishing temporary communication between a portable memory element and a microcontroller of the pressure-sensing system to communicate said pressure-sensing information to said portable memory element;
terminating communication between said portable memory element and said microcontroller; and
establishing communication between said portable memory element and said processing element to communicate said pressure-sensing information to said processing element.

11. A method for initializing electronics of a pressure-sensing syringe, the method comprising:
providing a syringe having a barrel, a plunger, a pressure transducer, an electrical circuit, a longitudinal adjustment mechanism, a threaded adjustment mechanism, and a locking mechanism, wherein said plunger comprises said pressure transducer and is positionable within and translatable along a length of said barrel, wherein said longitudinal adjustment mechanism is configured to selectively provide ingress and retraction of said plunger, and wherein said threaded adjustment mechanism is configured to selectively provide ingress and retraction of said plunger, and wherein said locking mechanism comprises a first position and a second position, said first position enabling use of said longitudinal adjustment mechanism and preventing use of said threaded adjustment mechanism, and said second position enabling use of said threaded adjustment mechanism and preventing use of said longitudinal adjustment mechanism;
using said syringe to obtain pressure-sensing information;
providing power to the electrical circuit;
determining whether an initial pressure monitored by said pressure transducer is within a range defined by at least one threshold value; and
reinitializing one or more components of the electrical circuit if the initial pressure is not within the range.

12. The method of claim 11, wherein the step of determining comprises determining whether the initial pressure is within an acceptable range for atmospheric pressures.

13. A syringe comprising:
a barrel;
a plunger positionable within and translatable along a length of the barrel;
a pressure transducer housed at least partially within an interior of the plunger;
a longitudinal adjustment mechanism configured to selectively provide ingress and retraction of said plunger;
a threaded adjustment mechanism configured to selectively provide ingress and retraction of said plunger;
a locking mechanism having a first position and a second position, wherein said first position disengages at least one thread of said locking mechanism to enable use of said longitudinal adjustment mechanism, and wherein said second position engages said at least one thread of said locking mechanism to enable use of said threaded adjustment mechanism; and
electronics in communication with the pressure transducer and located within a housing that is removably coupled to the syringe at a proximal end thereof.

14. The syringe of claim 13, wherein a plug removably couples the electronics to the syringe.

15. The syringe of claim 13, wherein the electronics and the housing are configured to be reused with another syringe.

16. A syringe comprising:
a barrel;
a plunger positionable within and translatable along a length of the barrel, wherein said plunger comprises a compliant element for sealing against an inner surface of said barrel of the syringe;
a pressure transducer housed at least partially within said plunger;
at least one element for securing said pressure transducer in place relative to the plunger;
a longitudinal adjustment mechanism configured to selectively provide ingress and retraction of said plunger;
a threaded adjustment mechanism configured to selectively provide ingress and retraction of said plunger; and
a locking mechanism having a first position and a second position, wherein said first position disengages at least one thread of said locking mechanism to enable use of said longitudinal adjustment mechanism, and wherein said second position engages said at least one thread of said locking mechanism to enable use of said threaded adjustment mechanism.

17. The syringe of claim 16, wherein said at least one element for securing comprises an end cap configured to engage or be engaged by a remainder of the plunger and to be assembled with said pressure transducer.

18. The syringe of claim 16, wherein said at least one element for securing includes a recess for receiving at least a portion of said compliant element.

19. The syringe of claim 17, wherein said at least one element for securing includes a pressure transmission element configured to communicate a pressure within the barrel of the syringe to said pressure transducer.

* * * * *